March 21, 1950 E. J. PFINGSTL Plant Pat. 927
CAMELLIA PLANT
Filed May 26, 1949
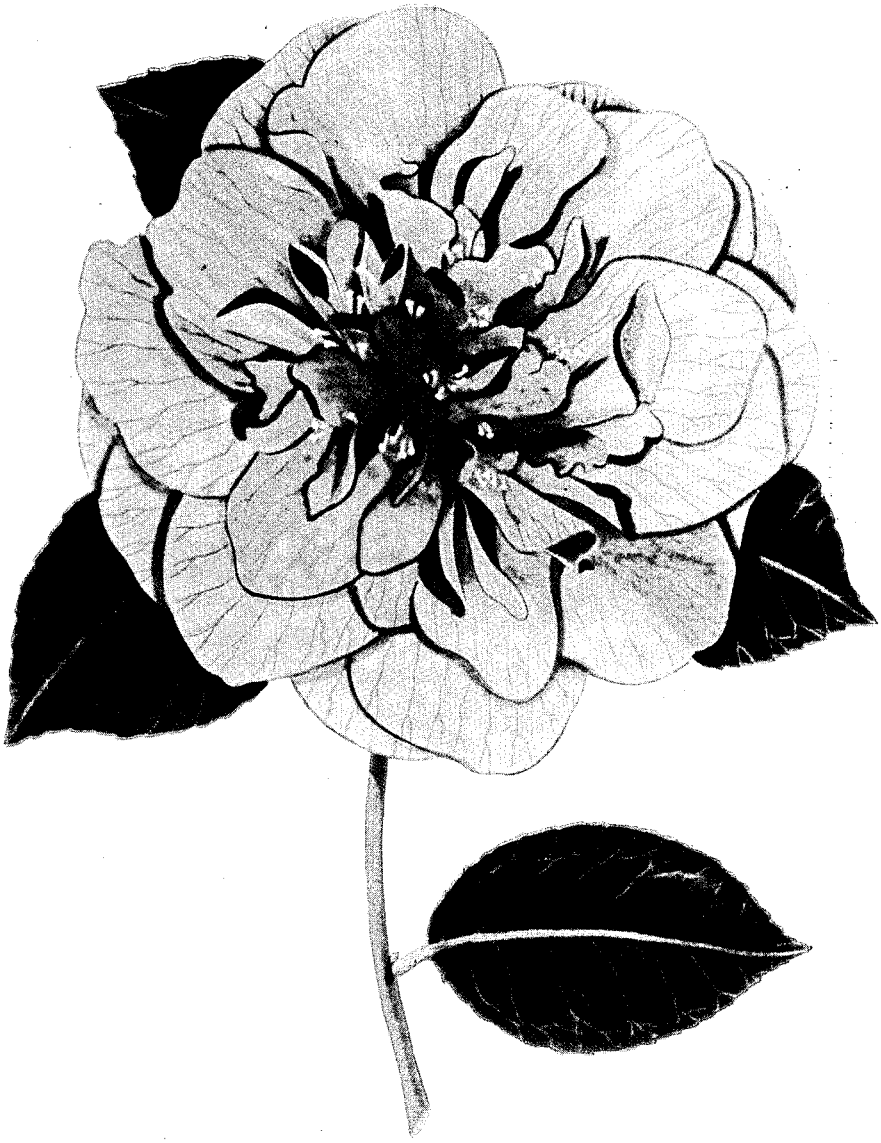
Inventor
E. J. Pfingstl
By Robbins Robb
Attorneys Patented Mar. 21, 1950

Plant Pat. 927

UNITED STATES PATENT OFFICE

927

CAMELLIA PLANT

Emmett J. Pfingstl, Montgomery, Ala.

Application May 26, 1949, Serial No. 95,519

1 Claim. (Cl. 47—60)

The present discovery relates to a new and distinct variety of camellia plant, originating as a seedling, of unknown parentage, selected from a large number of seedlings because it proved to be outstanding and distinct from any known variety of which I am aware.

This new camellia is characterized as to novelty by a combination of the following distinctive features:

(1) Most importantly, the blooming season, which extends from about the middle of October to about the first of April.

(2) The large size of the blooms, imbricated, formal and double.

(3) The form of the petals, the outer edges of which are waved and become fluted toward the center where they surround a group of yellow stamens and stand erect like rabbit ears; other stamens are intermixed with the petaloids. The effect of the erect central petaloids adds depth to the bloom, giving it somewhat of a hemispherical appearance.

(4) Vigorous, sturdy growth of the plant with large, broad, dark green serrated foliage.

(5) Hardiness and lasting quality of the blooms, holding their form and color well as a cut flower for days and on the plants for weeks, especially when grown in partial shade.

(6) Dark red color of blooms, showing no orange cast as in the case of similar dark red varieties.

So far as I know, the nearest like camellia is the variety "Victor Emanuel" (unpatented), but my new variety is distinguished from this known one in several important respects. "Victor Emanuel's" red color is suffused with orange coloring; it is a late bloomer and the stamens are all in the center whereas in the present variety they are interspersed with the petaloids, and the blooms have much more depth than the previously known variety referred to.

Asexual reproduction shows that the characteristics hold true through succeeding propagations.

Specimens were first asexually reproduced at Montgomery, Alabama, by cuttings and grafts.

In the drawing is shown a specimen of the bloom showing particularly the red coloring of the bloom as nearly as this can be depicted, the petaloid center and dispersion of the stamens at the center and about the petaloid area, together with specimens of the foliage, all of which characterize important novel features of this variety.

The following is a detailed description of the new variety, color terminology being in accordance with De Voe Artist Oil Colors, except where indicated to be in accordance with ordinary dictionary significance:

Parentage: Seedling of unknown parentage.

Classification: Botanic — *Camellia japonica* (woody plant).

Blooming habit: Early to late—October to April.

Bud:

*Size.*—Medium large.

*Form.*—Large, oval.

*Sepals.*—Broad, oval shape—4 to 6 in number; smooth edge. Color—Hookers Green (De Voe).

*Calyx.*—Shape—pear. Size—broad.

*Color when first opening.*—Rose Madder (De Voe).

Bloom: Size when fully open, large; 5 inches to 6 inches.

*Borne.*—Singly to stem; on strong, medium length stems.

*Form.*—When first petal opens—rose-like. When fully opened—incomplete double—petals on outer edge waved and become fluted toward the center.

*Petalage.*—Incomplete double; arranged irregularly.

*Color.*—Rose Madder (De Voe).

Petals: Thin; satiny.

*Shape.*—Oval.

*Arrangement.*—Irregular; informal; imbricated.

*Lasting quality.*—On plant—two to three weeks. As cut flower—five to six days.

Genital organs:

*Stamens, anthers.*—Medium size. Color—Chrome Yellow (Bronze Yellow). Arrangement—intermixed with petaloids.

*Stamens, filaments.*—Medium length. Color—yellow.

*Pollen.*—Color—yellow.

*Styles.*—Loosely separated; medium length.

*Ovaries.*—All enclosed in calyx.

Seed:

*Form.*—Ovoid.

*Aspect.*—Smooth.

*Color at maturity.*—Van Dyke Brown (De Voe).

*Sepals.*—Caducous; spear-shaped.

Form of plant: Bush; shrub.

Growth: Very vigorous; upright.

Foliage:

*Size.*—Large; serrated.

*Quantity.*—Normally abundant.

*Color.*—New foliage—Hooker's Green (De Voe). Old foliage—Dark Green; serrulated.

*Shape.*—Oval; pointed.

*Texture.*—Upper side—glossy; smooth; under side—smooth. Ribs and veins—prominent.

*Edge.*—Serrated.

Wood:

*New wood.*—Color—green.

*Old wood.*—Color—brown.

I claim:

A new and distinct variety of camellia plant characterized as to novelty by the exceptionally long blooming season; the large size, form and color of the blooms, including the form of the individual petals; the intermixture of erect petaloids and stamens; depth of the blooms; vigorous, sturdy habit of growth of hardy plants with large, broad, dark green, serrated foliage; and lasting qualities of the blooms on plant and as cut flowers, substantially as shown and described.

EMMETT J. PFINGSTL.

No references cited.